(12) United States Patent
Vartiainen (10) Patent No.: US 8,430,565 B2
(45) Date of Patent: Apr. 30, 2013

(54) X-RAY DEVICE HAVING HEAD STABILIZING MEMBER

(75) Inventor: Sami Vartiainen, Vantaa (FI)

(73) Assignee: PaloDEx Group Oy (FI)

( * ) Notice: Subject to any disclaimer, the term of this patent is extended or adjusted under 35 U.S.C. 154(b) by 347 days.

(21) Appl. No.: 12/792,263

(22) Filed: Jun. 2, 2010

(65) Prior Publication Data

US 2011/0299664 A1    Dec. 8, 2011

(51) Int. Cl.
*H05G 1/02* (2006.01)
(52) U.S. Cl.
USPC .................................................. 378/208
(58) Field of Classification Search ............... 378/20, 378/68, 38, 208
See application file for complete search history.

(56) References Cited

U.S. PATENT DOCUMENTS

| 3,673,408 | A | * | 6/1972 | Moss ................................ 378/39 |
| 5,224,140 | A | * | 6/1993 | Virta et al. ....................... 378/38 |
| 6,546,068 | B1 |  | 4/2003 | Shimura |
| 7,534,038 | B2 | * | 5/2009 | Rotondo et al. ............... 378/205 |
| 7,876,877 | B2 | * | 1/2011 | Stockl ............................. 378/38 |
| 2004/0013225 | A1 |  | 1/2004 | Gregerson et al. |
| 2004/0258195 | A1 |  | 12/2004 | Hara |
| 2005/0265523 | A1 |  | 12/2005 | Strobel |
| 2008/0137802 | A1 |  | 6/2008 | Suzuki et al. |
| 2009/0323891 | A1 |  | 12/2009 | Borghese et al. |

FOREIGN PATENT DOCUMENTS

| JP | 2004045212 A | 2/2004 |
| WO | 2006/013325 A1 | 2/2006 |
| WO | 2008/021671 A2 | 2/2008 |
| WO | 2010/037911 A1 | 4/2010 |

OTHER PUBLICATIONS

Web page for GENDEX Cone Beam 3-D Imaging; http://gendex.com/Default.aspx?navid=556740&oid=200&lid=us, last visited Jun. 30, 2010.
Web page for Next Generation i-CAT Product Images, Imaging Sciences International Inc.; http://www.imagingsciences.com/pro_iCAT_images_new.htm, last visited Jun. 30, 2010.

* cited by examiner

*Primary Examiner* — Irakli Kiknadze
(74) *Attorney, Agent, or Firm* — Andrus, Sceales, Starke & Sawall, LLP (57) ABSTRACT

An X-ray device includes a rotating unit that rotates an X-ray emitter and an opposing X-ray receiver about a patient's head. X-rays are emitted by the X-ray emitter and received by the X-ray receiver via the patient's head. An upper shelf supports the rotating unit. A head stabilizing member stabilizes the patient's head. The stabilizing member extends from a location adjacent to the rotating unit and above the X-ray emitter and X-ray receiver to a location wherein the patient's head is stabilized.

26 Claims, 8 Drawing Sheets

X-RAY DEVICE HAVING HEAD STABILIZING MEMBER

FIELD

The present disclosure relates to X-ray devices having a head stabilizing member, including but not limited to X-ray devices for extra-oral dental X-ray imaging.

BACKGROUND

Conventional extra-oral dental X-ray imaging devices typically include a mechanism that supports the patient's head in a stable position during imaging. In some examples, the mechanism includes a head support member hung from an upper shelf of the device. In these examples, the head support member is fed through a bearing assembly of a rotating unit on the device, thus requiring the main bearings to be relatively large so as to allow for bearing movement around the support member. Also, the rotating unit is an electronic component and therefore electrical cabling must be specially configured around the head supporting member. The present inventor has recognized that this type of arrangement is complex and expensive.

In other examples, the mechanism includes a head support member mounted on a lower shelf of the device. In these examples, the head support member does not interfere with the bearing and cabling mechanics; however, the support member must be relatively thin so as not to interfere with the X-ray process. The present inventor has recognized that this type of arrangement does not provide enough stable head support.

SUMMARY

The present disclosure provides X-ray devices. The devices include a rotating unit rotating an X-ray emitter and an opposing X-ray receiver about a patient's head, wherein X-rays are emitted by the X-ray emitter and received by the X-ray receiver via the patient's head. An upper shelf supports the rotating unit and a substantially vertical column supports the upper shelf. A head stabilizing member stabilizes the patient's head. The head stabilizing member extends from a location adjacent to the rotating unit and above the X-ray emitter and X-ray receiver to a location wherein the patient's head is stabilized.

DETAILED DESCRIPTION OF THE DRAWINGS

In the following description, certain terms have been used for brevity, clearness and understanding. No unnecessary limitations are to be implied therefrom beyond the requirement of the prior art because such terms are used for descriptive purposes only and are intended to be broadly construed. The different devices described herein may be used alone or in combination with other devices. It is to be expected that various equivalents, alternatives and modifications are possible within the scope of the appended claims. Each limitation in the appended claims is intended to invoke interpretation under 35 U.S.C. §112, sixth paragraph only if the terms "means for" are explicitly recited in the respective limitation.

Figure 1:
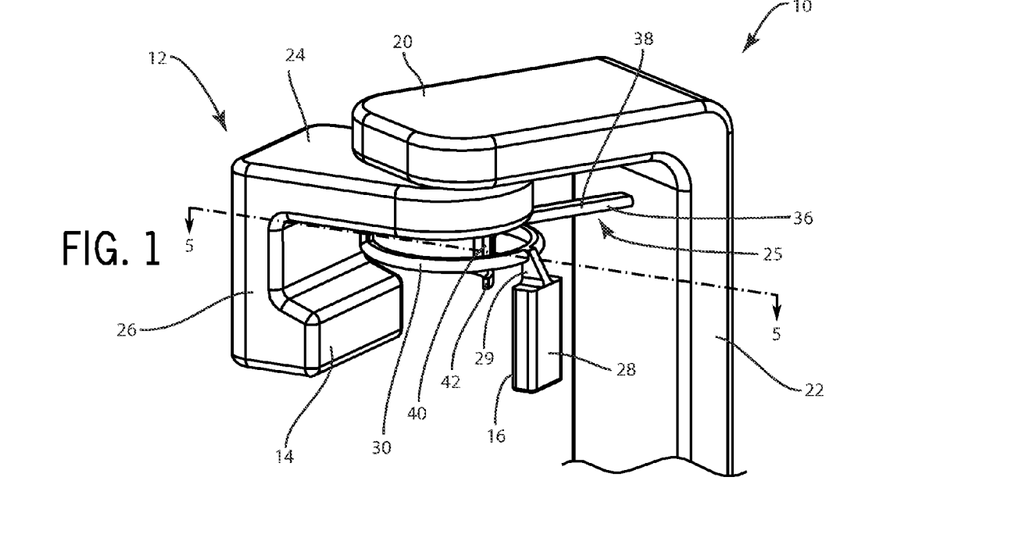
FIG. 1 is a perspective view of one embodiment of an X-ray device.
Figure 2:
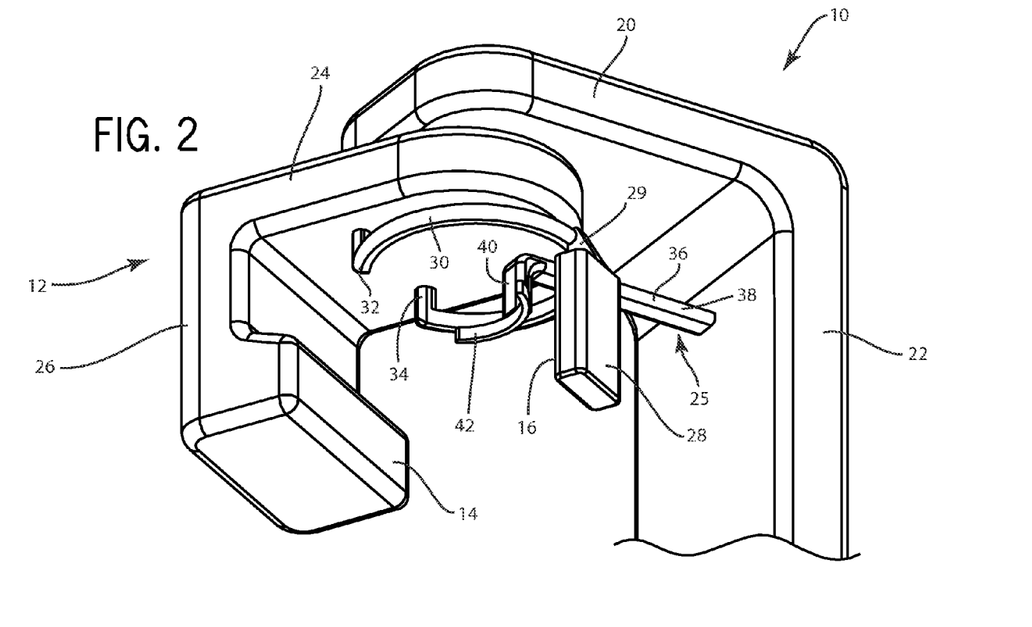
FIG. 2 is another perspective view of the X-ray device shown in FIG. 1.
Figure 3:
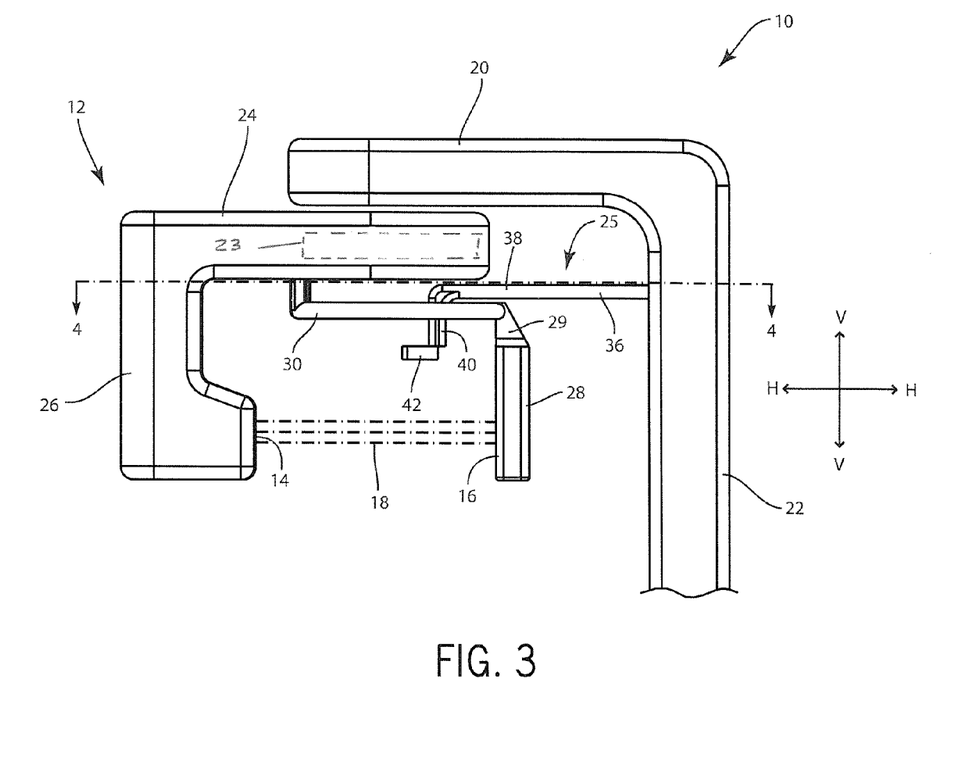
FIG. 3 is a side view of the X-ray device shown in FIG. 1.

FIGS. 1-5 depict one example of an X-ray device 10 configured as an extra-oral dental X-ray device. The device 10 includes a rotating unit 12 for rotating (as shown by arrow R in FIGS. 4 and 5) an X-ray emitter 14 and an opposing X-ray receiver 16 about a patient's head P. X-rays 18 (FIG. 3) are emitted by the X-ray emitter 14 and received by the X-ray receiver 16 via the patient's head P (FIGS. 4 and 5) to produce one or more X-ray images. The device 10 includes an upper shelf 20 supporting the rotating unit 12, and also a substantially vertical column 22 supporting the upper shelf 20. As shown in FIG. 3, the substantially vertical column 22 extends in a vertical direction V. The upper shelf 20 extends in a horizontal direction H that is generally perpendicular to the vertical direction V. In this manner, the substantially vertical column 22 and upper shelf 20 form an L-shape, wherein the upper shelf 20 extends from the vertical column 22 at a substantially right angle. The rotating unit 12 depends from and is located below the upper shelf 20 in the vertical direction V. The structure of the rotating unit, X-ray emitter, X-ray receiver, upper shelf, and support column can vary from that depicted in the drawings. For example, the vertical column 22 is not a necessary component. In other embodiments, the upper shelf 20 extends from a wall or other support structure rather than a column.

FIGS. 1-5 depict one example of an X-ray device 10 configured as an extra-oral dental X-ray device. The device 10 includes a rotating unit 12 for rotating (as shown by arrow R in FIGS. 4 and 5) an X-ray emitter 14 and an opposing X-ray receiver 16 about a patient's head at a location P. X-rays 18 (FIG. 3) are emitted by the X-ray emitter 14 and received by the X-ray receiver 16 via the patient's head (FIGS. 4 and 5) to produce one or more X-ray images. The device 10 includes an upper shelf 20 supporting the rotating unit 12, and also a substantially vertical column 22 supporting the upper shelf 20. As shown in FIG. 3, the substantially vertical column 22 extends in a vertical direction V. The upper shelf 20 extends in a horizontal direction H that is generally perpendicular to the vertical direction V. In this manner, the substantially vertical column 22 and upper shelf 20 form an L-shape, wherein the upper shelf 20 extends from the vertical column 22 at a substantially right angle. The rotating unit 12 depends from and is located below the upper shelf 20 in the vertical direction V. The structure of the rotating unit, X-ray emitter, X-ray receiver, upper shelf, and support column can vary from that depicted in the drawings. For example, the vertical column 22 is not a necessary component. In other embodiments, the upper shelf 20 extends from a wall or other support structure rather than a column.

In the example of FIGS. 1-5, the rotating unit 12 includes an upper housing 24 containing drive gears (not shown) and at least one bearing 23 for enacting such rotation. The rotating unit 12 further includes an emitter housing 26 carrying the X-ray emitter 14 and a receiver housing 28 carrying the opposing X-ray receiver 16. A support bar 30 is generally circular in shape and has opposing ends 32, 34 that are attached to and depending from the upper housing 24. The support bar 30 is located below the upper housing 24 and below the upper shelf 20 in the vertical direction V. The receiver housing 28 is attached to the circular support bar by a bracket 29. The structure of the upper housing, emitter housing, receiver housing and support bar can vary from that depicted in the drawings. Other non-limiting examples are shown in FIGS. 6-10, 11 and 12, discussed hereinbelow.

The device 10 further includes a head stabilizing member 25 for stabilizing the patient's head-P. The head stabilizing member 25 extends from a location adjacent to the rotating unit 12 and above the X-ray emitter 14 and X-ray receiver 16 in the vertical direction V to a location P where the patient's head is stabilized by the head stabilizing member 25. In the example shown in FIGS. 1-5, the head stabilizing member 25 includes an elongate member 36 having a first portion 38 and a second portion 40. In the example of FIGS. 1-5, the first portion 38 extends in the horizontal direction H from the substantially vertical column 22 to a location above the X-ray emitter 14 and X-ray receiver 16 in the vertical direction V and between the X-ray emitter 14 and X-ray receiver 16 in the horizontal direction H. The second portion 40 extends in the vertical direction V from the location above the X-ray emitter 14 and X-ray receiver 16 to a location P where the patient's head is stabilized. As shown in FIG. 3, the location P where the patient's head is stabilized is between the X-ray emitter 14 and X-ray receiver 16 in the horizontal direction H and level with the X-ray emitter 14 and X-ray receiver 16 in the vertical direction V. Thus the head stabilizing member 25 extends from the substantially vertical column 22 below the rotating unit 12 and above the X-rays emitted by the X-ray emitter 14. The head stabilizing member 25 does not have to be attached to the vertical column 22. For example, with reference to FIG. 11, the first portion 38 is connected to and extends from the upper shelf 20 in the vertical direction instead of the column 22 in the horizontal direction H. In another example that is not depicted, the head stabilizing member 25 extends from a wall supporting the upper shelf 20 and the vertical column is omitted. The structure and configuration of the head stabilizing member 25 can also vary from that shown.

In the example shown in FIGS. 1-5, the head stabilizing member 25 also includes a pad 42 located at the outer end of the second portion 40 of the elongate member 36. A sensor (not shown) can be co-located with the pad 42 for sensing a characteristic of the patients head. In this example, the elongate member 36 serves as a conduit for communication cables (not shown) for connecting the sensor to related control circuitry (not shown).

Figure 4:
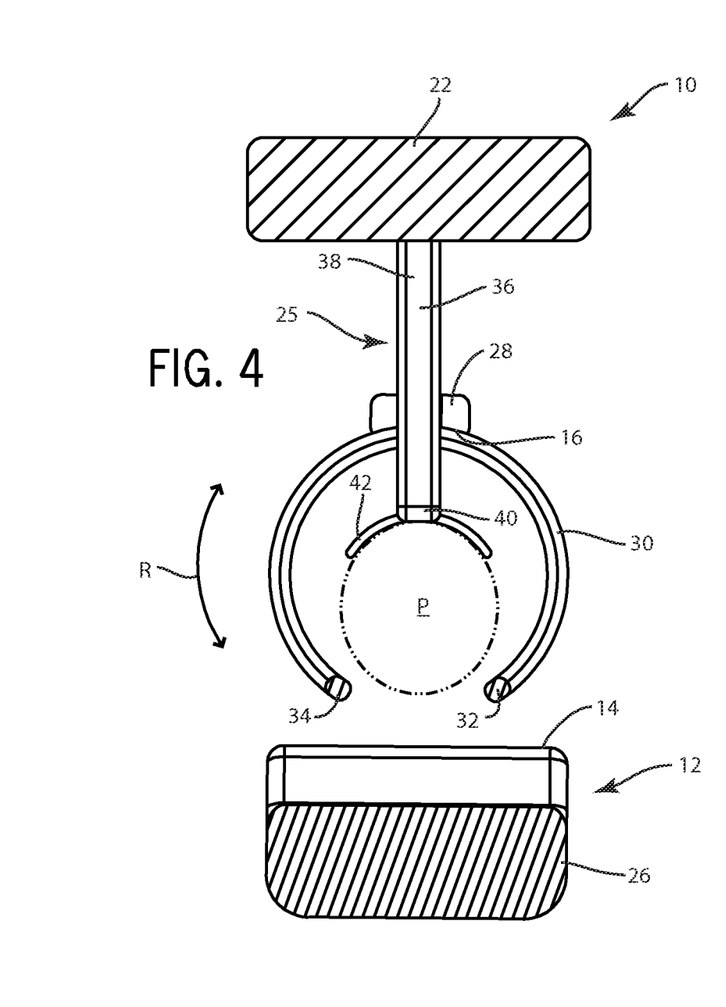
FIG. 4 is a view of Section 4-4 taken in FIG. 3.
Figure 5:
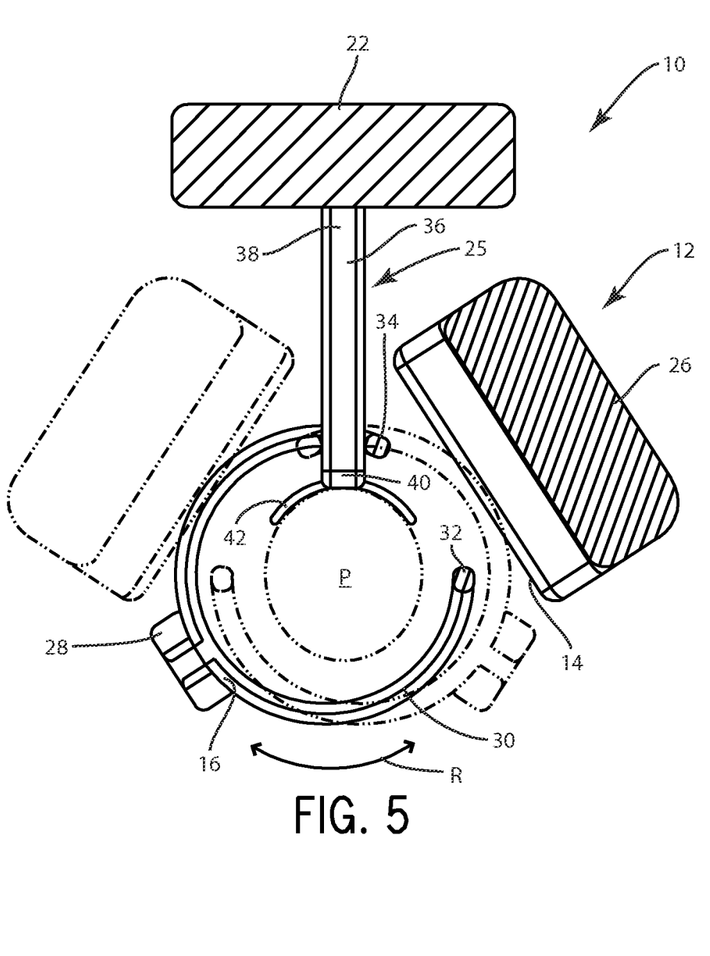
FIG. 5 is a view of Section 5-5 taken in FIG. 1 showing rotation of a rotating unit.
Figure 6:
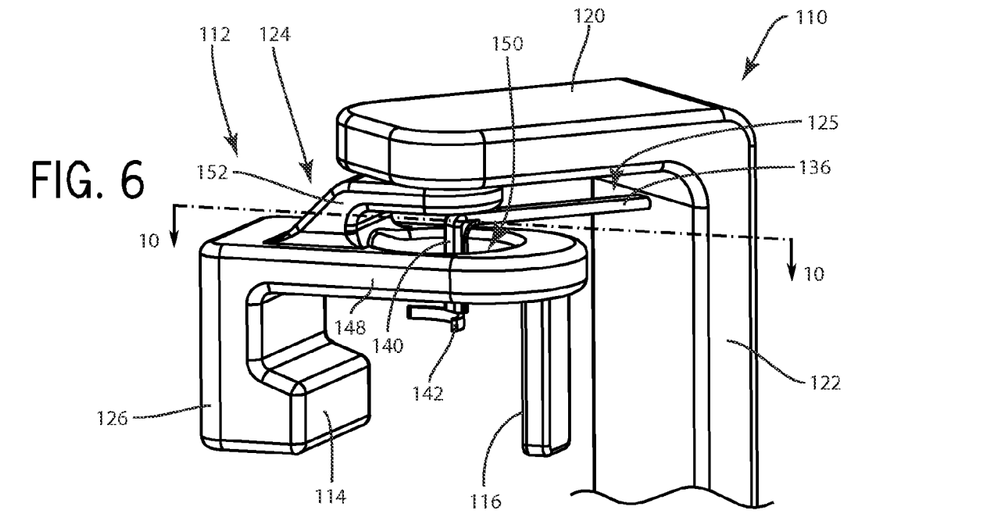
FIG. 6 is a perspective view of another embodiment of an X-ray device.
Figure 7:
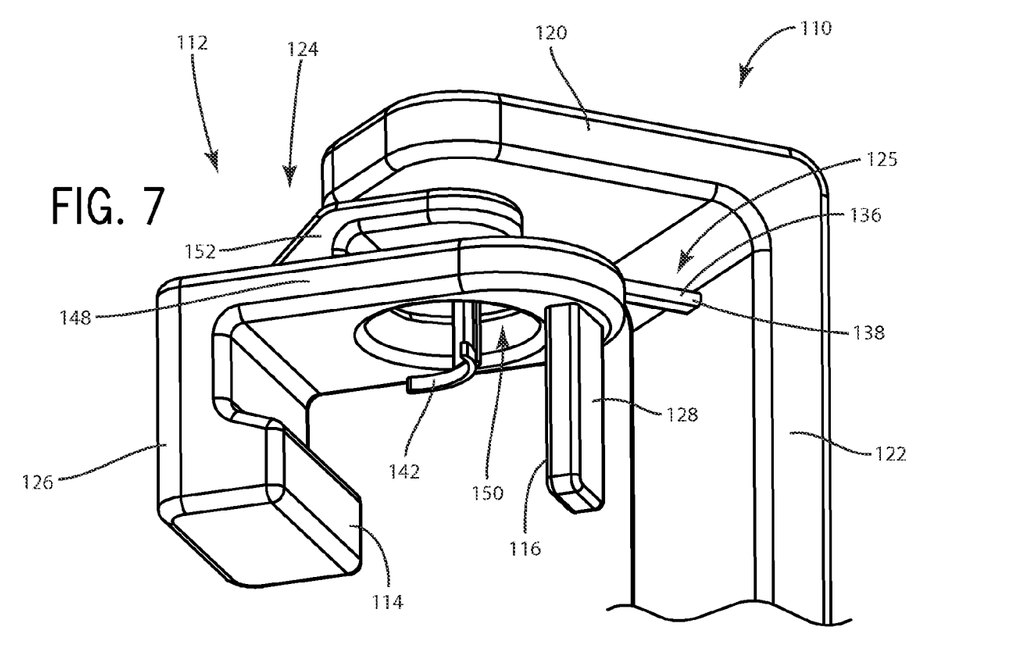
FIG. 7 is another perspective view of the X-ray device shown in FIG. 6.

As shown in FIGS. 4 and 5, the head stabilizing member 25 extends from a location adjacent to the rotating unit 12. In this example, the head stabilizing member 25 prevents full 360 degree rotation of the rotating unit 12 shown by arrow R. The limits of rotation of the rotating unit 12 occur where the opposing ends 32, 34 of the support bar 30 approach and engage with the head stabilizing member 25.

Figure 8:
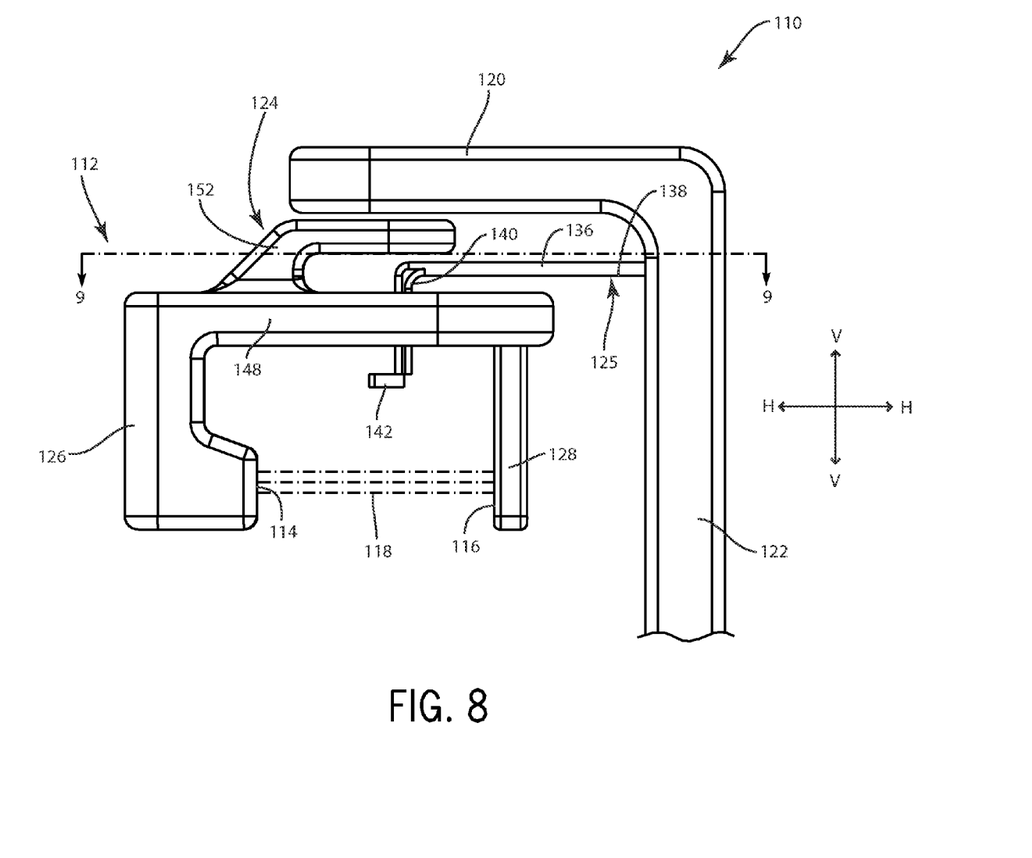
FIG. 8 is a side view of the X-ray device shown in FIG. 6.

FIGS. 6-10 depict another example of an X-ray device 110 configured as an extra-oral dental X-ray device. Similar to the device 10, the device 110 includes a rotating unit 112 for rotating (as shown by arrow R in FIGS. 9 and 10) an X-ray emitter 114 and an opposing X-ray receiver 116 about a patient's head. X-rays 118 are emitted by the X-ray emitter 114 and received by the X-ray receiver 116 via the patient's head to produce one or more X-ray images. The device 110 includes an upper shelf 120 supporting the rotating unit 112, and also a substantially vertical column 122 supporting the upper shelf 120. As shown in FIG. 8, the substantially vertical column 122 extends in a vertical direction V. The upper shelf 120 extends in a horizontal direction H that is generally perpendicular to the vertical direction V. In this manner, the substantially vertical column 122 and upper shelf 120 form an L-shape, wherein the upper shelf 120 extends from the vertical column 122 at a substantially right angle. The rotating unit 112 depends from and is located below the upper shelf 120 in the vertical direction V. The structure of the rotating unit, X-ray emitter, X-ray receiver, upper shelf, and support column can vary from that depicted in the drawings. As stated above, the vertical column 122 is not critical and is omitted in other embodiments.

In the example of FIGS. 6-10, the rotating unit 112 includes an upper housing 124 containing drive gears (not shown) for enacting such rotation. The rotating unit 112 further includes an emitter housing 126 carrying the X-ray emitter 114 and a receiver housing 128 carrying the opposing X-ray receiver 116. The upper housing 124 is directly connected to the emitter housing 126 by a transitional housing 152 and a support housing 148. The support housing 148 defines a central opening 150. As explained above, the structure of the upper housing, emitter housing, and receiver housing can vary from that depicted in the drawings.

Figure 9:
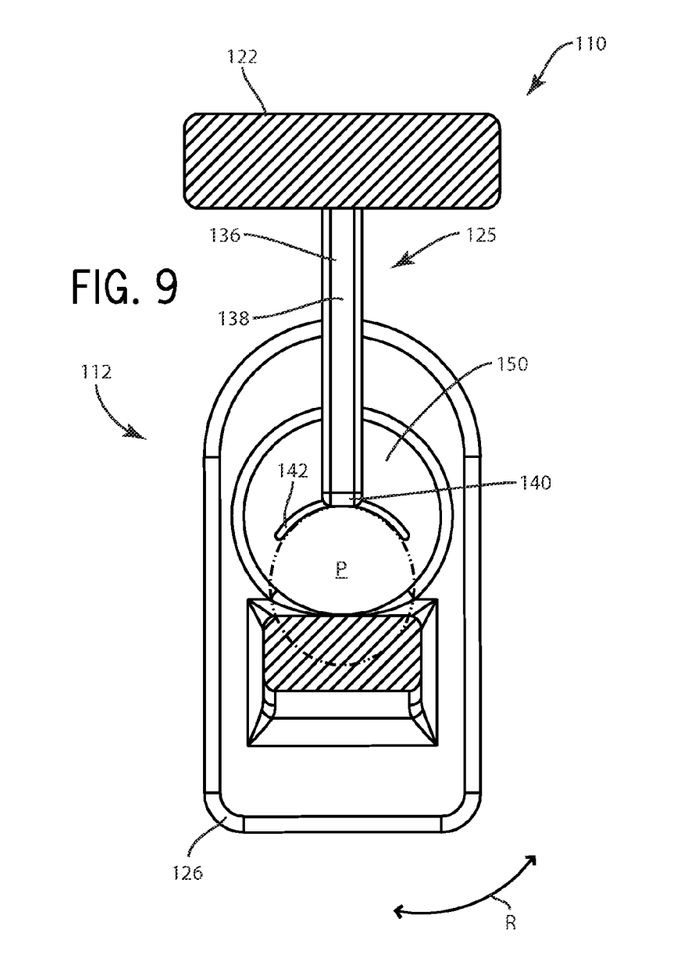
FIG. 9 is a view of Section 9-9 taken in FIG. 8.
Figure 10:
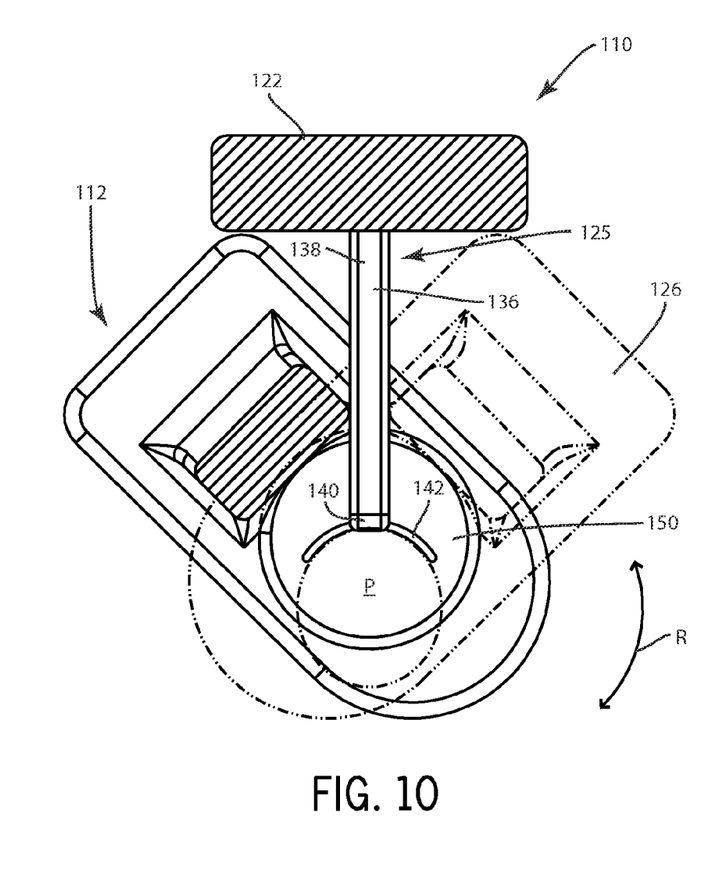
FIG. 10 is a view of Section 10-10 taken in FIG. 6 showing rotation of a rotating unit.
Figure 11:
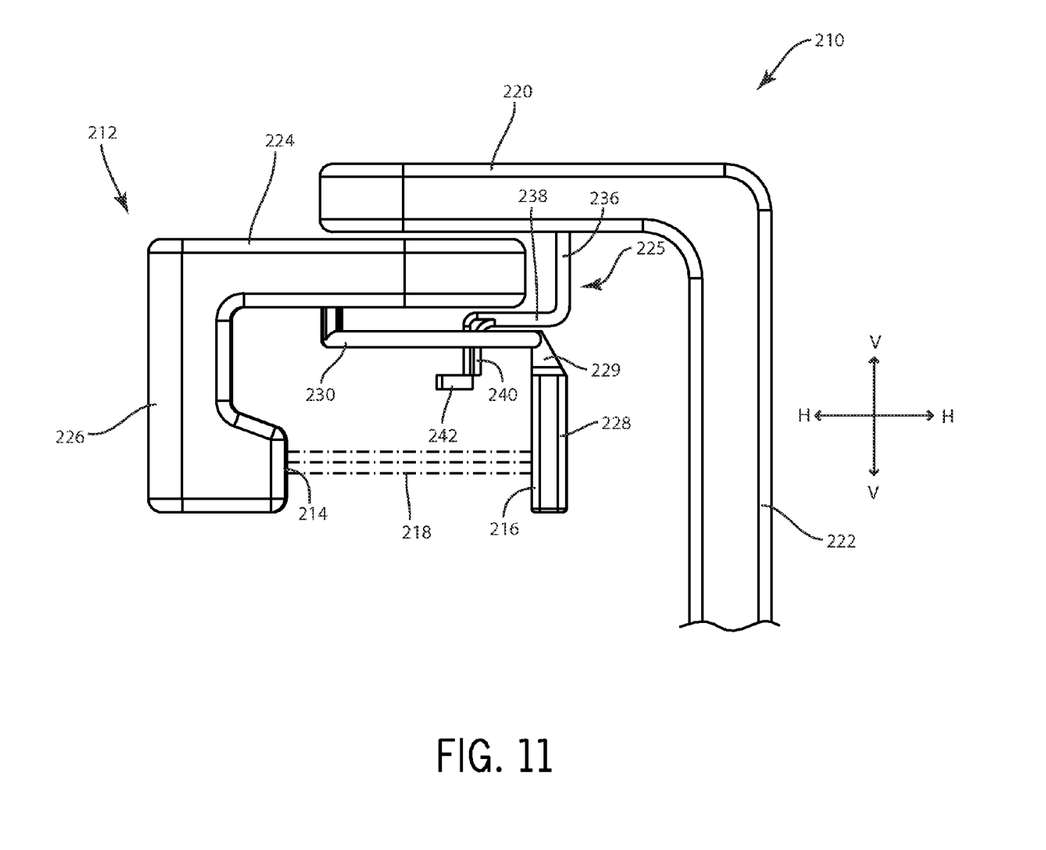
FIG. 11 is a side view of another embodiment of an X-ray device.

The device 110 further includes a head stabilizing member 125 for stabilizing the patient's head at the location P (FIGS. 9 and 10). The head stabilizing member 125 extends from a location adjacent to the rotating unit 112 and above the X-ray emitter 114 and X-ray receiver 116 to a location P where the patient's head is stabilized by the head stabilizing member 125. In the example shown, the head stabilizing member 125 includes an elongate member 136 having a first portion 138 and a second portion 140. The first portion 138 extends in the horizontal direction H from the substantially vertical column 122 to a location above the X-ray emitter 114 and X-ray receiver 116 in the vertical direction V and between the X-ray emitter 114 and X-ray receiver 116 in the horizontal direction H. The second portion 140 extends in the vertical direction V from the location above the X-ray emitter 114 and X-ray receiver 116 to a location P where the patient's head is stabilized. Specifically, the head stabilizing member 125 extends from a location above the opening 150, through the opening 150 and to the location P where the patient's head stabilized. In the example shown the location P where the patient's head is stabilized is between the X-ray emitter 114 and X-ray receiver in the horizontal direction H and level with the X-ray emitter 114 and X-ray receiver 116 in the vertical direction V. Thus the head stabilizing member 125 extends from the substantially vertical column 122 adjacent to the rotating unit, below the upper housing and above the X-rays 118 emitted by the X-ray emitter 114. In other examples, the first portion 138 can be connected to and extend from the upper shelf 120 in the vertical direction instead of the column 122 in the horizontal direction, for example as shown in FIG. 11. Also, the vertical column 122 can be omitted and the stabilizing member 125 can extend from e.g. a well or from the upper shelf 120. As explained above, the structure of the head stabilizing member 25 can vary from that shown.

In the example shown, the head stabilizing member 125 also includes a pad 142 located at the outer end of the second portion 140 of the elongate member 136. A sensor (not shown) can be co-located with the pad 142 for sensing a characteristic of the patients head. In this example, the elongate member 136 serves as a conduit for communication cables (not shown) for connecting the sensor to related control circuitry (not shown).

As shown in FIGS. 9 and 10, the head stabilizing member 125 extends from a location adjacent to the rotating unit 112. In this example, the head stabilizing member 125 prevents full 360 degree rotation of the rotating unit 112 shown by arrow R. The limits of rotation of the rotating unit 112 occur where the transitional housing 152 of the rotating unit 112 approaches and engages with the head stabilizing member 125.

Figure 12:
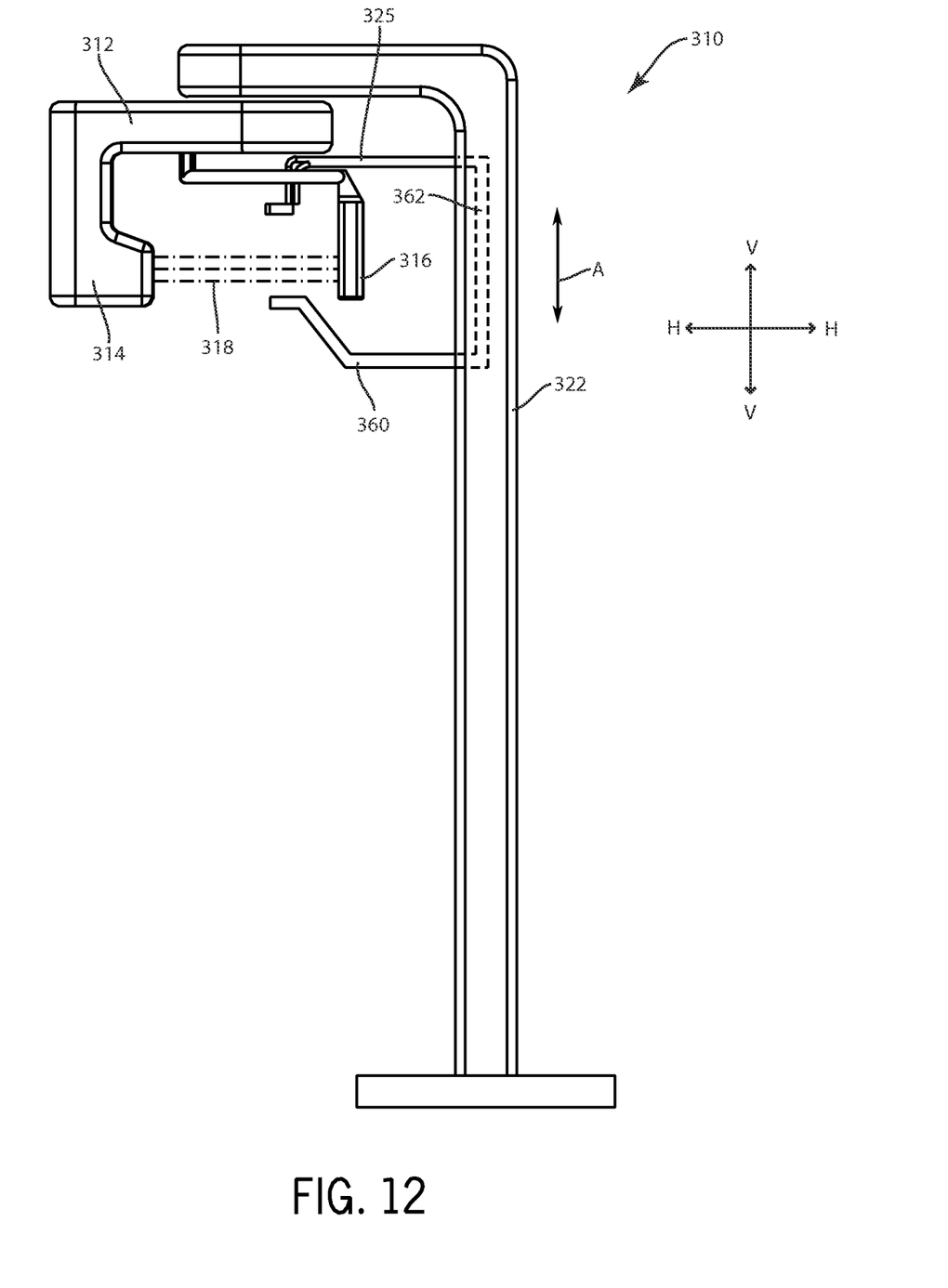
FIG. 12 is a side view of another embodiment of an X-ray device.

In the example of FIG. 12, the device 310 includes a head stabilizing member 325 for stabilizing the patient's head at location P. The head stabilizing member 325 extends from a location adjacent to the rotating unit 312 and above the X-ray emitter 314 and X-ray receiver 316 to the location P where the patient's head is stabilized by the head stabilizing member 325. The head stabilizing member 325 is connected to a chin stabilizing member 360. In the example shown, the head stabilizing member 325 and chin stabilizing member 360 are attached to or formed integral with a connection bar 362 that extends along the substantially vertical column 322 in the vertical direction V. In the example shown, the connection bar 362 extends within the vertical column 322; however, the connection bar 362 could be mounted to the outside of the column 322. Further, the column 322 can be omitted (as described previously) and the connection bar 362 can be mounted to a wall. In the example shown in FIG. 12, the chin stabilizing member 360 is movable in the vertical direction V as shown by arrow A. The head stabilizing member 325 is also movable as shown by arrow A. The head stabilizing member 325 and chin stabilizing member 360 are connected together and therefore can be moved simultaneously and in unison in the direction of arrow A. Conversely, the chin stabilizing member 360 and head stabilizing member 325 could be movable individually and separate from each other. Individual and/or collective movement of the respective members 360, 325 can be afforded by numerous mechanical connections such as slots, tracks or other functionally equivalent mechanical connections. Alternately, movement of the chin stabilizing member 360 and head stabilizing member 325 can be controlled by a drive mechanism and automated controller, as such mechanical and/or automated drive means are known in the art.

What is claimed is:

1. An X-ray device comprising:
a rotating unit configured to rotate an X-ray emitter and an opposing X-ray receiver about a patient's head having a head location, the X-ray emitter configured to emit X-rays toward the X-ray receiver through the patient's head;
an upper shelf; and
a bearing supported by the upper shelf and rotatably supporting the rotating unit; and
a head stabilizing member configured to stabilize the patient's head, the head stabilizing member extending from one of the upper shelf and a support structure for the upper shelf to the head location, wherein the head stabilizing member does not extend through the bearing.

2. An X-ray device according to claim 1, wherein the head stabilizing member extends from the upper shelf.

3. An X-ray device according to claim 1, wherein the support structure comprises a substantially vertical column supporting the upper shelf, wherein the head stabilizing member extends from the substantially vertical column to a location above the X-rays emitted by the X-ray emitter.

4. An X-ray device according to claim 1, wherein the head stabilizing member prevents the rotating unit from rotating 360 degrees.

5. An X-ray device according to claim 1, the head stabilizing member comprising an elongated member having a pad at one end adapted to receive a forehead of the patient's head.

6. An X-ray device according to claim 5, comprising a sensor on the pad adapted to sense a characteristic of the patent's head.

7. An X-ray device according to claim 6, the elongated member housing communication cables adapted to connect the sensor to control circuitry.

8. An X-ray device according to claim 1, wherein the support structure comprises a substantially vertical column supporting the upper shelf, wherein the head stabilizing member comprises a first portion that extends substantially perpendicularly to the substantially vertical column and a second portion that extends substantially parallel to the substantially vertical column.

9. An X-ray device according to claim 8, comprising a pad configured to rest on a patient's forehead, the pad being attached to the second portion.

10. An X-ray device according to claim 8, wherein the first portion extends from the substantially vertical column and the second portion extends from a location above the X-rays emitted by the X-ray emitter to the location where the patient's head is stabilized.

11. An X-ray device according to claim 1, comprising a chin stabilizing member configured to stabilize the patient's chin, wherein the head stabilizing member and chin stabilizing member are attached.

12. An X-ray device according to claim 11, wherein the chin stabilizing member and head stabilizing member are movable together in a height direction towards and away from the upper shelf to accommodate patients' heads of different sizes.

13. An X-ray device according to claim 11, wherein at least one of the chin stabilizing member and head stabilizing member are movable towards and away from the upper shelf and towards and away from the other of the chin stabilizing member and head stabilizing member to accommodate patients' heads of different sizes.

14. An X-ray device comprising:
a rotating unit configured to rotate an X-ray emitter and an opposing X-ray receiver about a patient's head, wherein X-rays are emitted by the X-ray emitter and received by the X-ray receiver via the patient's head;
an upper shelf configured to support the rotating unit; and
a head stabilizing member configured to stabilize the patient's head, the head stabilizing member extending from a location adjacent to the rotating unit and above the X-ray emitter and X-ray receiver to a location where the patient's head is stabilized;
a substantially vertical column supporting the upper shelf, the head stabilizing member extending from the substantially vertical column to the location where the patient's head is stabilized.

15. An X-ray device according to claim 14, wherein the head stabilizing member extends from the substantially vertical column to a location between the X-ray emitter and the opposing X-ray receiver.

16. An X-ray device according to claim 14, wherein the head stabilizing member extends from the substantially vertical column below the rotating unit and above the X-rays emitted by the X-ray emitter.

17. An X-ray device according to claim 14, wherein the upper shelf extends substantially perpendicularly horizontally from the substantially vertical column.

18. An X-ray device comprising:
- a rotating unit configured to rotate an X-ray emitter and an opposing X-ray receiver about a patient's head, wherein X-rays are emitted by the X-ray emitter and received by the X-ray receiver via the patient's head;
- an upper shelf configured to support the rotating unit; and
- a head stabilizing member configured to stabilize the patient's head, the head stabilizing member extending from a location adjacent to the rotating unit and above the X-ray emitter and X-ray receiver to a location where the patient's head is stabilized;
- the rotating unit comprising an upper housing containing drive gears configured to rotate the rotating unit, an emitter housing carrying the X-ray emitter, and a receiver housing carrying the X-ray receiver; wherein the head stabilizing member extends above the emitter housing and receiver housing but below the upper housing.

19. An X-ray device according to claim 18, wherein the upper housing is directly connected to the emitter housing.

20. An X-ray device according to claim 19, comprising a support bar connecting the upper housing to the receiver housing.

21. An X-ray device according to claim 20, wherein the support bar depends from the upper housing and the head stabilizing member extends between the support bar and the upper housing.

22. An X-ray device according to claim 21, wherein the support bar is circular and has opposing ends that depend from the upper housing.

23. An X-ray device according to claim 19, comprising a support housing connecting the emitter housing and the receiver housing.

24. An X-ray device according to claim 15, wherein the support housing comprises an opening, and the head stabilizing member extends between the upper housing and the support housing and through the opening in the support housing.

25. An X-ray device comprising:
- a rotating unit configured to rotate an X-ray emitter and an opposing X-ray receiver about a patient's head having a head location, the X-ray emitter configured to emit X-rays toward the X-ray receiver through the patient's head;
- an upper shelf;
- a bearing supported by the upper shelf and rotatably supporting the rotating unit;
- a head stabilizing member configured to stabilize the patient's head, wherein the head stabilizing member does not extend through the bearing; and
- a substantially vertical column supporting the upper shelf, the head stabilizing member extending from the substantially vertical column to the head location.

26. An X-ray device comprising:
- a rotating unit configured to rotate an X-ray emitter and an opposing X-ray receiver about a patient's head having a head location, the X-ray emitter configured to emit X-rays toward the X-ray receiver through the patient's head;
- an upper shelf;
- a bearing supported by the upper shelf and rotatably supporting the rotating unit; and
- a head stabilizing member configured to stabilize the patient's head, the head stabilizing member extending from one of the upper shelf and a support structure for the upper shelf to the head location, wherein the head stabilizing member does not extend through the bearing;
- the rotating unit comprising an upper housing containing drive gears configured to rotate the rotating unit, an emitter housing carrying the X-ray emitter, and a receiver housing carrying the X-ray receiver; wherein the head stabilizing member extends above the emitter housing and receiver housing but below the upper housing.

* * * * *